United States Patent
Lindsey et al.

(10) Patent No.: US 8,057,651 B1
(45) Date of Patent: Nov. 15, 2011

(54) ELECTROCHEMICAL SENSOR WITH NANO-WIRE ARRAY

(75) Inventors: Norris Lindsey, Suitland, MD (US); Appajosula Yashodhara Rao, Bethesda, MD (US); Appajosula Srinivasa Rao, Bethesda, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 853 days.

(21) Appl. No.: 12/154,811

(22) Filed: May 15, 2008

(51) Int. Cl.
*G01N 17/04* (2006.01)
(52) U.S. Cl. ......... 204/404; 977/762; 977/781; 977/813
(58) Field of Classification Search .................. 204/404, 204/280, 286.1; 977/762, 781, 785, 813
See application file for complete search history.

(56) References Cited

U.S. PATENT DOCUMENTS

| | | | | |
|---|---|---|---|---|
| 2,918,420 | A * | 12/1959 | Sabins | 204/196.06 |
| 6,185,961 | B1 | 2/2001 | Tonucci et al. | |
| 6,187,165 | B1 | 2/2001 | Chien et al. | |
| 6,231,744 | B1 * | 5/2001 | Ying et al. | 205/324 |
| 7,190,049 | B2 | 3/2007 | Tuominen et al. | |

OTHER PUBLICATIONS

SSPC-VIS 3 Visual Standard for Power- and Hand-Tool Cleaned Steel. (Standard Reference Photographs) Guide and Standard, SSPC 93-04, Steel Structures Paint Council, Pittsburgh, PA 15213-3728.

* cited by examiner

*Primary Examiner* — Jeffrey T Barton
*Assistant Examiner* — J. Christopher Ball
(74) *Attorney, Agent, or Firm* — Richard A. Morgan

(57) ABSTRACT

An electro-chemical sensor comprises a bismuth nano-wire array. The sensor is used to detect incipient corrosion under paint. It is particularly useful in admiralty and marine applications such as for detecting incipient metal oxidation such as rusting and for monitoring the progress of metal oxidation on ship hulls and tanks. It is also useful in the automobile industry for quantifying surface quality in preparation for painting.

18 Claims, No Drawings

ELECTROCHEMICAL SENSOR WITH NANO-WIRE ARRAY

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

1. Field of the Invention

The invention relates to an electro-chemical sensor such as a corrosion sensor including an array of bismuth nano-wires extending through a chemically inert, non-conductive membrane.

2. Discussion of the Related Art

Methods have been developed that for the fabrication of bismuth nano-wire arrays. Bismuth nano-wire arrays have been grown by electro-deposition on a nano-porous template. Nano-pores are formed in the template by controlled bombardment with swift heavy ions to produce ion tracks. The ion tracks are etched to the desired nano-diameter. The templates have been used to produce arrays of parallel nano-wires that are up to 10 micrometers in length. Etching of the template is controlled so that wires are produced with single nanometer to micron diameters. Density of nano-wires in the array can be varied from about $10^4$ wires/mm$^2$ to $10^7$ wires/mm$^2$.

Nano-porous templates have been fabricated from glass, mica, alumina and polycarbonate polymer. Commercially available nano-porous materials that can be used for templates include porous aluminum oxide (Anopore®), ion-track-etched polycarbonate (Nuclepore®) and ion-track-etched mica.

Detection of corrosion on ship hulls and tanks is of continuing interest in the marine and the admiralty. It is known that paint is not entirely effective in preventing rust from forming on a hull or tank in a corrosive sea water environment. Rust can occur under the paint, undetected prior to forming a blister. Prior to blistering rusting goes on undetected. After blistering, when time permits, the paint is removed and the surface inspected. Pre-blistering paint removal is not usually done on ship hulls and tanks. Also, the quality of any visual inspection is dependent on the thoroughness of the paint removal. It would be desirable to detect insipient rusting under the paint, before blistering and damage occurs. An apparatus for detecting insipient rusting would not achieve wide acceptance if it interfered with the hydrodynamic stream line of the ship hull or added to the acoustic signature of a naval vessel.

Inventors have discovered that the challenge of detecting insipient rusting can be solved by a new electro-chemical sensor.

SUMMARY OF THE INVENTION

The invention is an electro-chemical sensor. The sensor comprises a bismuth nano-wire array in a nano-capillary insulating membrane. The nano-wires have a work piece contact end and a base end. The nano-wire base ends are in contact with a bismuth film on a surface of the insulating membrane. An electric potential measuring means is in electrical contact with the bismuth film.

The electro-chemical sensor is packaged so that it is electrically and chemically insulated and attached directly to a clean ferrous metal surface such as a hull or tank surface. Paint is applied to the hull or tank over the sensor. The sensor is so thin that it is visually detectable only by lead wires connecting it to a measuring means such a potentiometer in the ship control room.

DETAILED DESCRIPTION OF THE INVENTION

The electro-chemical sensor of the invention relies on a nano-wire array. The nano-wire array is a nano-capillary membrane containing up to $10^7$ essentially parallel nano-wires per square millimeter. Wires produced by deposition on an ion-track-etched template are essentially cylindrical, varying in diameter from single nanometers (nm) or microns (mµ) up to millimeters (mm) in magnitude. The wires are functionally parallel in that they do not contact each other. Nano-wire produced from a template with less regularly shaped nano-capillary walls, such as in an aluminum oxide (alumina) membrane or in a non-woven fiber membrane, has a shape corresponding with that template.

It is conventional to refer to both nanometer diameter wires and micrometer (micron) diameter wires as nano-wires. Likewise, when used in a general, non quantitative sense, the term nano is intended herein to include the term micron.

Inventors were searching for a corrosion detector for naval ship structural metals, particularly iron, aluminum, copper and copper-nickel alloys. The detector metal must be more reactive than the detected metal. Bismuth is capable of removing oxygen from iron (including steel), aluminum and copper (including copper-nickel alloys). In the case of rusted steel two alternative reactions are possible. Bismuth reacts with ferric oxide to form bismuth oxide and ferrous oxide according to the reaction:

$$Bi+Fe(3+) \rightarrow Bi(3+)+Fe(2+).$$

In the alternative, bismuth reacts with ferric oxide to form bismuth oxide and iron according to the reaction:

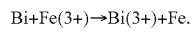

$$Bi+Fe(3+) \rightarrow Bi(3+)+Fe.$$

Experimental measurements were made with a silver/silver chloride reference electrode cell and computer controlled potentiostat. A potentiostat is an electronic instrument that controls the voltage difference between a working electrode and a reference electrode.

As a result of experimentation, bismuth was selected as the nano-wire material. As referred to herein, bismuth is a bismuth-containing material selected from the group consisting of elemental bismuth (Bi) and bismuth telluride (Bi$_2$Te$_3$). Also contemplated as nano-wire materials are bismuth alloys that are active in removing oxygen from iron (including steel), aluminum, copper and copper-nickel alloys.

An advantage of the invention is the size of the sensor. The smaller the size of the nano-wire in contact with the iron-containing surface, the greater the sensitivity of the measurement. The above-described redox reaction takes place at the tip of a nano-wire at the interface where the wire contacts the work piece. The limiting case is the reaction at a single nano-wire detecting the reaction between iron oxide molecules and bismuth atoms there. For practical considerations, 30 or more nano-wires per sensor, preferably 30 to 60 nano-wires per sensor for a nano-size sensor. This provides for the detection of 30 to 60 sites of iron oxide molecules reacting bismuth atoms. Assuming the nano-wire lattice comprises a wire spacing of about 0.3 nanometers (nm), 30 to 60 nano-wires will be contained in 10 to 20 nm$^2$.

Template nano-capillaries are formed by ion bombardment followed by track etching. For example, 10 micron thick mica was bombarded with 15 MeV C$^{4+}$ ions at a density of $10^{11}$ to $10^{13}$ ions/cm$^2$. Bombardment creates tracks in the mica. Subsequent etching with hydrofluoric acid (HF) creates through-the-thickness nano-capillaries of uniform diameter. Pore diameter is refined by varying etching time and temperature. For example, a diameter of 8 nanometers (nm) is achievable.

Ion-track-etched templates are commercially available for a number of materials useful for the invention. Ion-track-etched membranes of mica, glass, mica, alumina, and polymers, e.g. polycarbonate and polyethylene, having a thickness suitable for use to grow a bismuth nano-wire array.

Muscovite mica is sold by Asheville-Schoomaker Mica Co., Newport News, Va. Cleaved sheets of 7 to 8 micron thickness and surface areas of about 100 cm$^2$ are commercially available.

Commercially available track-etched membranes include those sold under the trademark NUCLEPORE® from Whatman, Inc., Newton, Mass. NUCLEPORE® track-etched membranes are manufactured from high grade polycarbonate film. These membranes have high chemical resistance and high tensile strength. These polycarbonate membranes are available in film thicknesses ranging from 6 micrometers to 11 micrometers and in pore sizes ranging from 0.0015 micrometers (1.5 nanometers) to 12.0 micrometers.

Polymer templates are contemplated which are made of polymers including polycarbonate, polyethylene terephthalate, polypropylene, polyvinylidene-fluoride, polyimide, polymethylmethacrylate, polystyrene and block copolymers thereof.

Inventors have discovered that nano-porous non-woven fiber sheets are an effective template. Nano-porous non-woven fiber sheets are a commercially available filter membrane, often referred to in the art as filter paper. It is essential to understand that not all nano-porous non-woven fiber sheets are useful for the invention. Only those fiber sheets that have porosity due to through-the-thickness capillary pores are useful because the capillary is the template for nano-wires. Some non-woven fiber sheets have nano-porosity due to layering of fiber without any direct through-the-thickness porosity. Such fiber sheets are not useful for the invention. Applicants have found through-the-thickness nano-porous non-woven fiber sheets to be cost effective and therefore preferred.

Non-woven fiber sheet is preferably hydrophilic so that it does not interfere with ion transport. Filaments for a making a hydrophilic nano-porous fiber sheet are made from a polymer such as polypropylene, polyethylene, polyamide polyester, polyfluorocarbon, polyacrylonitrile, polyurethane, and the like and block copolymers thereof. Additionally cellulose, lingo-cellulose and block copolymers thereof are used. Sheets are available in thicknesses of about 0.1 to about 2 millimeter (mm) thickness and pore sizes down to about 1 to 2 microns and up to 100 microns in diameter. Preferably the pore sizes, and hence the wire diameters range about 0.1 to 20 microns, most preferably about 0.1 to 1 micron. Also preferred are thicknesses of about 0.1 to 10 microns. Filter paper having a thickness of about 0.1 millimeter and average pore diameter of about 50 nanometers has also been found to be effective. Final selection of wire diameter is based on effectiveness for the intended use.

Another template for growing a nano-wire is glass. The diameter of glass capillaries in a template ranges typically from 100 microns to 1 millimeter (mm). The length ranges typically from 0.01 to 0.1 microns.

In order to grow a nano-wire array, one surface of the template is provided with a working electrode. The working electrode is a film of an electrically conducting material which, under influence of an electromotive force, can move material into the channels of the template. The side of the template that is covered with the conducting material is perpendicular to the disposition of the channels and the coating is a thin film on the order of magnitude of up to about one micron in thickness, typically 0.1 to 1 micron, more typically 0.1 to 0.5 micron. The material applied to one side of the template is electrically conducting and is most effectively a metal selected from the group including platinum, palladium, gold, silver, nickel, chromium or copper. Inventors have found that copper is preferred based on performance in forming bismuth nano-wires. The metal can be deposited on the membrane surface by methods including thin film sputtering, thermal evaporation, and electron-beam evaporation.

The thin film coating applied to the template should not be too thick or too thin and should have sufficient adhesion to stick to a membrane surface. If the coating is too thick, it may crack or peel. If the coating is too thin, it may not produce nano-wires because the nano-capillaries in the membrane are not sufficiently covered for nano-wire growth. All of the nano-capillary ends must be covered.

The nano-wires are fabricated from a bismuth-containing material selected from the group including substantially pure elemental bismuth and bismuth telluride. Equivalent bismuth alloys are contemplated. The discrete nano-wires may be deposited by techniques known in the art, such as electroplating, electrochemical deposition, chemical vapor deposition and ion-assisted deposition. U.S. Pat. No. 6,187,165 for Arrays of Semi-Metallic Bismuth Nanowires and Fabrication Techniques Therefor by C. Chien is incorporated herein by reference as one teaching for fabricating a bismuth nano-wire array.

An electrical connection is established with the film coating by securing a metal wire or strip thereto and leading the strip or wire outside the electroplating tank where it is connected to an electrical source. The material and the electrical connection are then electrically isolated to assure that during electroplating, deposition of the material is made directly in the nano-capillaries of the template and not elsewhere.

An electroplating apparatus is one of the means that can be used to fill the capillaries in the ion-track-etched template with bismuth metal. The ion-track-etched template is placed in an electroplating solution. Salts of bismuth are dissolved in distilled water with a small amount of nitric acid to produce bismuth ions ($Bi^{3+}$) in the electroplating solution. If the nano-wires are to include tellurium, the electroplating solution must also include salts of tellurium to provide tellurium ions ($Te^{4-}$). The counter electrode, typically a standard silver/silver chloride reference electrode, is disposed opposite and spaced from the nano-capillary track-etched membrane. The counter electrode is electrically connected to the coating on the nano-capillary ion-track-etched template through an electrical power source which applies an electromotive force between the counter electrode and the thin film coating of the nano-capillary track-etched template in the form of a voltage differential which serves to drive metal cations from the plating solution into the channels of the nano-capillary track-etched template.

Progress of the electroplating can be monitored by following the current displayed by a reference electrode. The reference electrode can be of the same material as the counter electrode, but need not be. The reference electrode is electrically connected to the counter electrode. A voltmeter and ammeter are used to monitor the voltage and current in the electroplating solution.

The voltage applied by the voltage source is fixed in the range of 115 to 125 millivolts. Depending on many factors, the electroplating process typically takes 1 to 20 hours, more typically 2 to 10 hours, for the channels to fill with bismuth metal. If the applied voltage is too low, no electroplating will take place and the channels will remain empty. Deposition in the channels will be slow if the applied voltage is too low. If the applied voltage is too high, deposition of the material in the channels will take place quickly and it is imperative to discontinue the electroplating process to avoid over filling the channels and forming a layer of bismuth metal on the opposite side of the template from the working electrode surface. If the applied voltage is too high and deposition of the material is too fast, granular or porous, non-smooth wires may be produced. It has been found that electroplating can be continued until the growing bismuth wires protrude from the template surface, and then terminated before electroplating of the template surface occurs. It is desirable that the wires extend beyond the template surface for contact with a work piece. Inventors have achieved wire extensions beyond the template of 0.01 to 0.1 millimeters in the laboratory. Inventors consider that the extensions already achieved can be exceeded. After growth of the nano-wires is complete, the working electrode is removed from the template by etching. The template remains with the nano-wires and serves as the insulating membrane of the electro-chemical sensor.

The nano-wire array is a nano-capillary membrane containing up to $10^7$ essentially parallel nano-wires per square millimeter of varying pattern configuration with the wire diameters. The wires are essentially cylindrical, varying in diameter from single nanometers (nm) to micron (μm) size. The ratio of length to width is up to about 10,000. Center-to-center spacing of the wires is up to about 30 diameters to less than 0.5 diameters. Typically, the array contains $10^4$ to $10^7$ wires per square millimeter which are 8 nanometers (nm) to 10 millimeters in diameter, typical length of 0.01 to 0.1 millimeter (mm) and spacing of 0.5 to 20 diameters. U.S. Pat. No. 6,185,961 for Nanopost Arrays and Process for Making Same to R. J. Tonucci et al. is incorporated herein by reference.

The bismuth nano-wire array is packaged for use as an electro-chemical sensor. The working electrode is replaced with a minimal coating of bismuth metal to establish electrical contact with the bismuth nano-wires. About 1 to 2 nanometers of coating is operative. However, 0.1 millimeters to 10 microns is preferred. In practice, copper tape is applied to the bismuth film. An aluminum tape backing is applied for strength and then an insulating tape, such as poly (tetra-fluoro ethylene) tape, e.g. Teflon® tape. After the nano-wire array is packaged for use, the thickness of the resulting electro-chemical sensor is determined by the thickness of the tape backing and packaging selected. That is, the bismuth nano-wires and support membrane are much thinner than the supporting tape backing. If packaging thickness is a consideration, the thickness can be reduced by the application of an insulating epoxy paint, coating or adhesive layer instead of one or more tape layers. For example, inventors have used the epoxy ethyl-2-cyanoacrylate, sold under trademark KRAZY GLUE®, as a packaging material.

The ferrous metal ship hull is prepared by grit blasting or water jet blast cleaning. The surface is inspected to assure that all rust is gone. The packaged bismuth nano-wire array is applied with the nano-wire ends in contact with the cleaned hull and then painted over to hold the package in place. An electric potential measuring means, e.g. a potentiometer is connected to the sensor through a lead wire attached to the bismuth coating layer. Electric potential between the bismuth and the ferrous hull is monitored. Insipient rusting is detected by resistance to current between ferric oxide rust and a bismuth nano-wire. Open circuit current is indicative of oxide ions transported from the ferric oxide to the contact surface of a bismuth nano-wire.

The hand held sensor fabricated in Example 2 has utility in the automobile industry for quantifying surface quality in preparation for painting. In this application a sensor would be calibrated to detect a phosphate film on a cleaned steel surface prior to the application of paint.

This invention is shown by way of example.

Example 1

Bismuth nano-wires were grown by electroplating in 1 millimeter (mm) diameter capillaries in a glass membrane substrate. The working electrode was copper tape and the reference electrode was a silver/silver chloride reference electrode. Deposition of bismuth from a solution containing bismuth (III) ions continued for 20,000 seconds. The nano-wire was photographed under a Scanning Electron Microscope (SEM). Photographs showed fine flake crystalline bismuth.

Example 2

A nano-wire array was formed by electro-chemical deposition of bismuth on Anopore® filter paper. The nano-wire array was attached to a graphite electrode to form a portable, hand held electro-chemical sensor.

The electro-chemical sensor was contacted with rust samples. Rusting was quantified by resistance to current readings at the bismuth nano-wire end to rust contact. The following measurements were made on a first sample.
Clean surface: 0.3 Mega ohms.
Very thinly rusted surface: 5 Mega ohms.
Slightly rusted surface: 8 Mega ohms.
Partially rusted surface: 12 Mega ohms.
Heavily rusted surface: greater than 20 Mega ohms.
Ceramic coated surface: greater than 20 Mega ohms.
Measurements were made on a second sample.
Clean surface: 5.7 Mega ohms.
Slightly rusted surface: 8 Mega ohms.
Partially rusted surface: 12 Mega ohms.
Heavily rusted surface: 19 Mega ohms.

All rust descriptions were made with reference to SSPC-VIS 3 *Visual Standard For Power- and Hand-Tool Cleaned Steel*, (Standard Reference Photographs) Guide and Standard, SSPC 93-04, Steel Structures Painting Council, Pittsburgh, Pa. 15213-3728.

This data provided a semi-quantitative calibration of the sensor. The full range of operation of the sensor was 0.0 Mega ohms to 20.0 Mega ohms. A 0.0 Mega ohm reading produced for a clean surface and a 20.0 Mega ohm reading for a heavily rusted surface. The ceramic coated surface measurement was included in the Example to demonstrate the detector's response to complete resistance to current flow, such as presented by a very heavily rusted surface. The data confirmed this.

It is apparent that the sensor has utility in the automobile industry for quantifying surface quality in preparation for painting auto bodies.

The foregoing discussion discloses and describes embodiments of the invention by way of example. One skilled in the art will readily recognize from this discussion, that various changes, modifications and variations can be made therein without departing from the spirit and scope of the invention as defined in the following claims.

What is claimed is:
1. An electro-chemical sensor comprising:
(a.) a nano-wire array comprising:

(i.) an insulating membrane having a work piece contact surface and a base surface and parallel nano-capillaries extending there through, and
(ii.) essentially parallel bismuth nano-wires that do not contact each other, each bismuth nano-wire in the nano-wire array extending within a nano-capillary from 0.01 to 0.1 millimeters beyond the work piece contact surface to the base surface,
(iii.) each bismuth nano-wire comprising micron size crystals grown in the nano-capillary by electroplating,
(b.) a bismuth film, coating the base surface and in contact with the bismuth nano-wires,
(c.) electric potential measuring means in electrical contact with the bismuth film.

2. The electro-chemical sensor of claim 1 wherein the bismuth nano-wires and the bismuth film are both made from a metal selected from the group consisting of elemental bismuth and bismuth telluride.

3. The electro-chemical sensor of claim 1 wherein the bismuth nano-wires have a diameter of 8 nanometers to 10 millimeters.

4. The electro-chemical sensor of claim 1 wherein the bismuth nano-wires have a length of 0.01 to 10 millimeters.

5. The electro-chemical sensor of claim 1 wherein the insulating membrane is made of a material selected from the group consisting of fiber, polymer, glass, mica and alumina.

6. The electro-chemical sensor of claim 1 wherein the electric potential measuring means is in electrical contact with both the bismuth film and a work piece, the work piece having on its surface an element selected from the group consisting of iron, aluminum and copper.

7. The electro-chemical sensor of claim 1 wherein the electric potential measuring means is in electrical contact with both the bismuth film and a ferrous work piece.

8. The electro-chemical sensor of claim 1 wherein the bismuth nano-wires comprise bismuth (III) crystals having an average size of 1 to 10 microns.

9. An electro-chemical sensor comprising:
(a.) a nano-wire array comprising:
(i.) a non-woven fiber insulating membrane having a work piece contact surface and a base surface and a plurality nano-capillaries extending there through, and
(ii.) a plurality of bismuth nano-wires, each nano-wire in the plurality of essentially parallel bismuth nano-wires that do not contact each other extending within a capillary from 0.01 to 0.1 millimeters beyond the work piece contact surface to the base surface,
(iii.) the bismuth nano-wires comprising crystals grown by electroplating and having an average crystal size of 1 to 10 microns,
(b.) a bismuth film, coating the base surface and in contact with the plurality of bismuth nano-wires,
(c.) electric potential measuring means in electrical contact with the bismuth film.

10. The electro-chemical sensor of claim 9 wherein the bismuth nano-wires and the bismuth film are both made from a metal selected from the group consisting of elemental bismuth and bismuth telluride.

11. The electro-chemical sensor of claim 9 wherein the bismuth nano-wires have a diameter of 0.1 to 20 microns.

12. The electro-chemical sensor of claim 9 wherein the bismuth nano-wires have a diameter of 0.1 to 1 microns.

13. The electro-chemical sensor of claim 9 wherein the bismuth nano-wires have a length of 0.1 to 10 microns.

14. The electro-chemical sensor of claim 9 wherein the non-woven fiber insulating membrane is nano-porous filter paper.

15. The electro-chemical sensor of claim 9 wherein the electric potential measuring means is in electrical contact with both the bismuth film and a work piece, the work piece having on its surface a metal element selected from the group consisting of iron, aluminum and copper.

16. The electro-chemical sensor of claim 9 wherein the electric potential measuring means is in electrical contact with both the bismuth film and a ferrous work piece.

17. The electro-chemical sensor of claim 9 wherein the bismuth nano-wires comprise sub micron size bismuth (III) crystals.

18. The electro-chemical sensor of claim 1 wherein the bismuth nano-wires comprise sub micron size bismuth (III) crystals.

\* \* \* \* \*